United States Patent [19]

Drabek

[11] Patent Number: 4,698,358

[45] Date of Patent: Oct. 6, 1987

[54] USE OF 3-ACYLAMINOBENZISOTHIAZOLES FOR CONTROLLING PESTS

[75] Inventor: Jozef Drabek, Oberwil, Switzerland

[73] Assignee: Ciba-Geigy Corporation, Ardsley, N.Y.

[21] Appl. No.: 896,562

[22] Filed: Aug. 13, 1986

Related U.S. Application Data

[63] Continuation of Ser. No. 637,086, Aug. 2, 1984, abandoned.

[30] Foreign Application Priority Data

Aug. 9, 1983 [CH] Switzerland .................. 4335/83

[51] Int. Cl.[4] .................... A01N 43/80; C07D 275/04
[52] U.S. Cl. ...................................... 514/373; 548/212
[58] Field of Search .................. 548/212; 514/373

[56] References Cited

U.S. PATENT DOCUMENTS 3,692,795  9/1972  Böshagen ........................ 548/212
3,707,364 12/1972  Becke ............................... 548/212

FOREIGN PATENT DOCUMENTS 0191734  2/1986  European Pat. Off. ........... 514/373
3544436  6/1986  Fed. Rep. of Germany ...... 514/373
1125872  9/1918  United Kingdom ............... 548/214

OTHER PUBLICATIONS

Theodora W. Greene, "Protective Groups in Organic Synthesis," John Wiley & Sons, New York (1981), p. 163.
J. F. W. McOmie, "Protective Groups in Organic Chemistry", Plenum Press, New York (1973), pp. 53–54.
George W. Ware, "Pesticides Theory and Application"W. H. Freeman and Co., San Francisco (1972)—pp. 18 & 281 (1983).

Primary Examiner—Donald G. Daus
Assistant Examiner—Barbara Cassatt
Attorney, Agent, or Firm—Edward McC. Roberts; Kevin T. Mansfield

[57] ABSTRACT

The use in pest control of 3-acrylaminobenzisothiazoles of the formula I

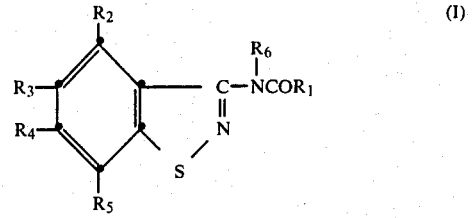

wherein $R_1$ is unsubstituted or substituted alkyl or phenyl, $R_2$, $R_3$, $R_4$ and $R_5$ independently of one another are each hydrogen, halogen, $C_1$–$C_5$-alkyl, $C_1$–$C_5$-alkoxy, trifluoromethyl, amino or nitro, and $R_6$ is hydrogen or —$COR_1$.

There are also described the novel compounds of the formula Ia

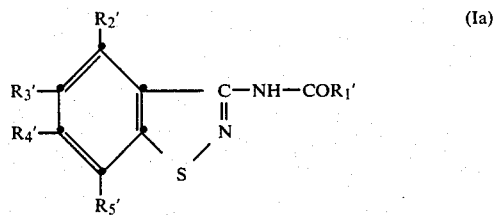

wherein
$R_1'$ is $C_1$–$C_{10}$-alkyl substituted by halogen or by $C_1$–$C_5$-alkoxy, or is unsubstituted $C_2$–$C_{10}$-alkyl or phenyl,
$R_2'$, $R_3'$, $R_4'$ and $R_5'$ independently of one another are each hydrogen, halogen, $C_1$–$C_5$-alkyl, $C_1$–$C_5$-alkoxy, trifluoromethyl, amino or nitro, and
$R_6'$ is hydrogen or —$COR_1'$; or
$R_1'$ is methyl,
$R_2'$, $R_3'$, $R_4'$ and $R_5'$ independently of one another are each hydrogen, halogen, $C_1$–$C_5$-alkyl, $C_1$–$C_5$-alkoxy, trifluoromethyl, amino or nitro, and
$R_6'$ is hydrogen; or
$R_1'$ is methyl,
$R_2'$ is hydrogen, $C_1$–$C_5$-alkyl, $C_1$–$C_5$-alkoxy, trifluoromethyl, amino or nitro,
$R_3'$, $R_4'$ and $R_5'$ independently of one another are each hydrogen, trifluoromethyl, amino or nitro, and
$R_6'$ is —$COR_1'$;

and also described are pesticidal compositions containing, as active ingredients, compounds of the formulae I and Ia, as well as processes for producing these 2-acylaminobenzisothiazoles.

5 Claims, No Drawings

USE OF 3-ACYLAMINOBENZISOTHIAZOLES FOR CONTROLLING PESTS

This application is a continuation of application Ser. No. 637,086, filed Aug. 2, 1984, now abandoned.

The present invention relates to the use of 3-acylaminobenzisothiazoles for controlling pests, to compositions containing such 3-acylaminobenzisothiazoles as active ingredients, to the novel 3-acylaminobenzisothiazoles and to processes for producing them.

The 3-acylaminobenzisothazoles to be used according to the invention have the formula

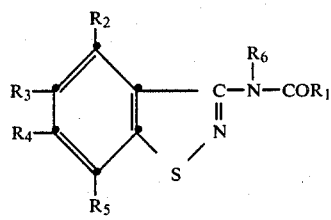

(I)

wherein $R_1$ is unsubstituted or substituted alkyl or phenyl, $R_2$, $R_3$, $R_4$ and $R_5$ independently of one another are each hydrogen, halogen, $C_1$-$C_5$-alkyl, $C_1$-$C_5$-alkoxy, trifluoromethyl, amino or nitro, and $R_6$ is hydrogen or —$COR_1$.

The compounds of the formula I can also be in their tautomeric form of the formula

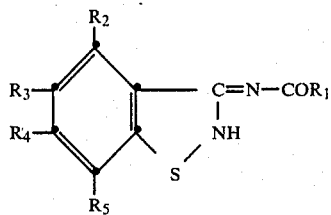

when $R_6$ is hydrogen.

By halogen is meant in this case fluorine, chlorine, bromine or iodine, especially chlorine or fluorine.

The alkyl and alkoxy groups denoted by $R_1$ to $R_5$ can be straight-chain or branched-chain. The $R_1$ alkyl groups have 1 to 10, preferably 1 to 5, carbon atoms.

Examples of substituents on the alkyl and phenyl groups in the case of $R_1$ are, inter alia: halogen, $C_1$-$C_5$-alkoxy, amino, nitro and/or trifluoromethyl.

Examples of alkoxy groups and unsubstituted or substituted alkyl groups denoted by $R_1$ to $R_5$ are, inter alia: methyl, methoxy, —$CH_2Cl$, trifluoromethyl, ethyl, ethoxy, —$CH_2CH_2F$, —$CF_2CF_3$, propyl, —$CF_2$—$CF_2$—$CF_3$, isopropyl, n-, i-, sec- or tert-butyl, n-pentyl, n-hexyl and n-decyl, and isomers thereof.

The compound of the formula

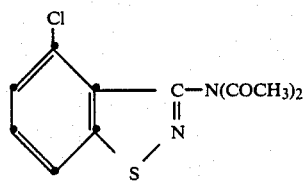

is described as herbicide in the German Offenlegungsschrift No. 1,915,387.

Preferred compounds are the novel compounds of the formula Ia

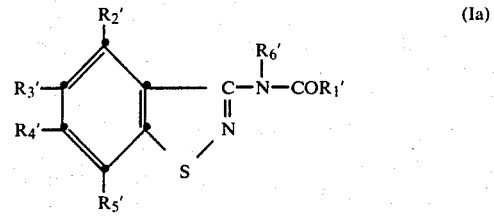

(Ia)

wherein
$R_1'$ is $C_1$-$C_{10}$-alkyl substituted by halogen or by -$C_1$-$C_5$-alkoxy, or is unsubstituted $C_2$-$C_{10}$-alkyl or phenyl,
$R_2'$, $R_3'$, $R_4'$ and $R_5'$ independently of one another are each hydrogen, halogen, $C_1$-$C_5$-alkyl, $C_1$-$C_5$-alkoxy, trifluoromethyl, amino or nitro, and
$R_6'$ is hydrogen or
$R_1'$ is methyl,
$R_2'$, $R_3'$, $R_4'$ and $R_5'$ independently of one another are each hydrogen, halogen, $C_1$-$C_5$-alkoxy, trifluoromethyl, amino or nitro, and
$R_6'$ is hydrogen; or
$R_1'$ is methyl,
$R_2'$ is hydrogen, $C_1$-$C_5$-alkoxy, trifluoromethyl, amino or nitro,
$R_3'$, $R_4'$ and $R_5'$ independently of one another are each hydrogen, trifluoromethyl, amino or nitro, and
$R_6'$ is —$COR_1'$.

Particularly preferred are compounds of the formula Ia wherein
$R_1'$ is $C_1$-$C_5$-alkyl substituted by fluorine or chlorine, or is unsubstituted $C_2$-$C_5$-alkyl,
$R_2'$, $R_3'$, $R_4'$ and $R_5'$ independently of one another are each hydrogen, chlorine, methyl, trifluoromethyl, amino or nitro, and
$R_6'$ is hydrogen or —$COR_1'$; or
$R_1'$ is methyl,
$R_2'$, $R_3'$, $R_4'$ and $R_5'$ independently of one another are each hydrogen, chlorine, methyl, trifluoromethyl, amino or nitro, and
$R_6'$ is hydrogen; or
$R_1'$ is methyl,
$R_2'$ is hydrogen, $C_1$-$C_5$-alkyl, $C_1$-$C_5$-alkoxy, trifluoromethyl, amino or nitro,
$R_3'$, $R_4'$ and $R_5'$ independently of one another are each hydrogen, chlorine, methyl, trifluoromethyl, amino or nitoro, and
$R_6'$ is —$COR_1$.

The compounds of the formula Ia, which can also be in their tautomeric form of the formula

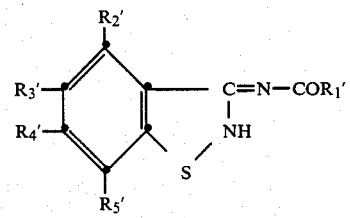

(when R6' is hydrogen), are produced by methods known per se, for example as follows:

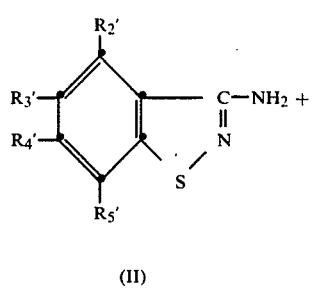

(II)

ClCOR1' $\xrightarrow[\text{in the presence of a base}]{\text{optionally}}$ Ia, wherein R6' is hydrogen (III)

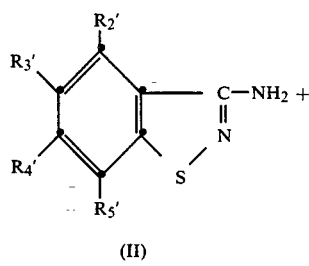

(II)

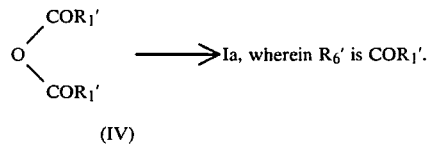

(IV)

In the formulae II, III and IV, the symbols $R_1'$ to $R_5'$ have the meanings defined under the formula Ia. The compounds of the formula I are produced in an analogous manner.

Suitable bases are in particular tertiary amines, such as trialkylamines, dialkylanilines and p-dialkylaminopyridines.

The processes are performed under normal pressure, at a temperature of −25° to 150° C., preferably at 50° to 100° C., and optionally in a solvent or diluent.

Solvents or diluents which are suitable are for example: ethers and ethereal compounds, such as diethyl ether, diisopropyl ether, dioxane and tetrahydrofuran; aromatic hydrocarbons, such as benzene, toluene and xylenes; ketones, such as acetone, methyl ethyl ketone and cyclohexanone; nitriles, such as acetonitrile, esters, such as ethyl acetate and butyl acetate; as well as dimethylforamide, dimethyl sulfoxide, methyl cyanide and halogenated hydrocarbons.

The compounds of the formula II can also be in their tautomeric form of the formula

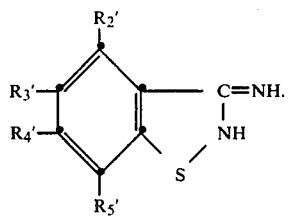

The starting materials of the formulae II, III and IV are known and can be produced by known processes.

The compounds of the formulae I and Ia are suitable for controlling pests on animals and plants, as well as in the soil.

The compounds of the formulae I and Ia are particularly suitable for controlling insects, for example of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera; and also mites and ticks of the order Acarina.

Compounds of the formulae I and Ia are especially suitable for controlling insects that damage plants, in particular insects that damage plants by eating, in crops of ornamental plants and productive plants, particulary in cotton and rice crops (for example *Spodoptera littoralis, Heliothis virescens, Chilo suppressalis* and *Laodelphax*); and also in vegetable and fruit crops (for example against *Leptinotarsa decemlineata, Myzus persucae, Laspeyresia pomonella* and *Adoxophyes reticulana*); and for controlling soil insects (for example *Aulacophora femoralis, Chortophila brassicae, Diabrotica balteata, Pachnoda savigni* and *Scotia ypsilon*).

Active substances of the formulae I and Ia exhibit a very favourable action also against flies, for example *Musca domestica*, and against mosquito larvae.

The acaricidal and insecticidal action of the novel compounds of the formulae I and Ia can be substantially broadened and adapted to suit the prevailing conditions by the addition of other insecticides and/or acaricides. Suitable additives are for example: organic phosphorus compounds, nitrophenols and derivatives thereof, formamidines, ureas, other pyrethrin-like compounds, as well as carbamates and chlorinated hydrocarbons.

Compounds of the formulae I and Ia are combined particularly advantageously also with substances having a synergistic or intensifying effect on pyrethroids. Examples of such compounds are, inter alia: piperonylbutoxide, propynyl ethers, propynyl oximes, propynyl carbamates and propynyl phosphonates, 2-(3,4-methylenedioxyphenoxy)-3,6,9-trioxaundecane (Sesamex or Sesoxane), S,S,S-tributylphosphorotrithioates and 1,2-methylenedioxy-4-(2-(octylsulfinyl)-propyl)-benzene.

The compounds of the formulae I and Ia are used either in an unmodified form or preferably together with auxiliaries customarily employed in formulation practice, and are thus processed in a known manner for example into the form of emulsion concentrates, directly sprayable or dilutable solutions, diluted emulsions, wettable powders, soluble powders, dusts or granulates, and also encapsulations in for example polymeric substances. The application processes, such as spraying, atomising, dusting, scattering or pouring, and likewise the type of composition, are selected to suit the objectives to be achieved and the given conditions.

The formulations, that is to say, the compositions or preparations containing the active ingredients of the formulae I and Ia, and optionally a solid or liquid additive, are produced in a known manner, for example by the intimate mixing and/or grinding of the active ingredients with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutyl-or dioctylphthalate, aliphatic hydrocarbons, such as cyclohexane or paraffins, alcohols and glycols, as well as ethers and esters thereof, such as ethanol, ethylene glycol, ethylene glycol monomethyl or-ethyl ethers, ketones such as cyclohexanone, strongly polar solvents, such as N-methyl-2-pyrrolidone, dimethyl sulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acid or highly dispersed absorbent polymers. Suitable granulated adsorptive carriers are porous types, for example pumice, ground brick, sepiolite or bentonite, and suitable nonsorbent carriers are materials such as calcite or sand. There can also be used a great number of pregranulated materials of inorganic or organic nature, such as in particular dolomite or ground plant residues.

Depending on the nature of the active ingredients of the formulae I and Ia to be formulated, suitable surface-active compounds are: nonionic, cationic and/or anionic tensides having good emulsifying, dispersing and wetting properties. By 'tensides' are also meant mixture of tensides.

Suitable anionic tensides are both so-called water-soluble soaps as well as water-soluble, synthetic, surface-active compounds.

Soaps which are applicable are the alkali metal, alkaline-earth metal or optionally substituted ammonium salts of higher fatty acids ($C_{10}$–$C_{22}$), for example the Na or K salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and in general contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included amongst these are also the salts of sulfuric acid esters and of sulfonic acids of fatty alcohol ethylene oxide adducts. The sulfonated benzimidazole derivatives preferably contain 2 sulfonic acid groups and a fatty acid group having 8-22 C atoms. Alkylarylsulfonates are for example the Na, Ca or triethanolamine salts of dodecylbenzenesulfonic acid, of dibutylnaphthalenesulfonic acid, or of a naphthalenesulfonic acid-formaldehyde condensation product. Also suitable are corresponding phosphates, for example salts of the phosphoric ester of a p-nonylphenol-(4–14)-ethylene oxide adduct, and phospholipides.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonioic tensides which may be mentioned are: nonylphenol-polyethoxyethanols, castor oil polyglycol ethers, polypropylene/polyethyleneoxy adducts, tributylphenoxy-polyethoxyethanol, polyethylene glycol and octylphenoxy-polyethoxyethaol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyltrimethylammonium chloride or benzyldi(2-chloroethyl)ethylammonium bromide.

The tensides customarily used in formulation practice are described, inter alia, in the following publications:
"Mc Cutcheon's Detergents and Emulsifiers Annual", MC Publishing Corp., Ridgewood, N.J., 1982; and
Dr. Helmut Stache "Tensid Taschenbuch", Carl Hanser Verlag, Munich/Vienna, 1981.

The pesticidal preparations contain as a rule 0.1 to 99%, particularly 0.1 to 95%, of an active ingredient of the formula I or Ia, 1 to 99.9% of a solid or liquid additive, and 0 to 25%, especially 0.1 to 25%, of a tenside.

Whereas commercial products are preferably in the form of concentrated compositions, the preparations employed by the end-user have as a rule a considerably lower concentration of active ingredient.

The compositions can also contain further additives, such as stabilisers, antifoaming agents, viscosity regulators, binders and adhesives, as well as ferilisers or other active ingredients for obtaining special effects.

FORMULATION EXAMPLES FOR LIQUID ACTIVE INGREDIENTS OF THE FORMULAE I AND IA (%=PERCENT BY WEIGHT)

| 1. Emulsion concentrates | (a) | (b) | (c) |
| --- | --- | --- | --- |
| active ingredient | 25% | 40% | 50% |
| calcium dodecylbenzenesulfonate | 5% | 8% | 6% |
| castor oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of the required concentration can be produced from these concentrates by dilution with water.

| 2. Granulates | (a) | (b) |
|---|---|---|
| active ingredient | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is then evaporated off in vacuo.

| 3. Dusts | (a) | (b) |
|---|---|---|
| active ingredient | 2% | 5% |
| highly dispersed silicic acid | 1% | 5% |
| talcum | 97% | — |
| kaolin | — | 90% |

Dusts ready for use are obtained by the intimate mixing together of the carriers with the active ingredient.

FORMULATION EXAMPLE FOR SOLID ACTIVE INGREDIENTS OF THE FORMULAE I AND IA (%=PERCENT BY WEIGHT)

| 4. Wettable powders | (a) | (b) | (c) |
|---|---|---|---|
| active ingredient | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7-8 mols of ethylene oxide) | — | 2% | — |
| highly dispersed silicic acid | 5% | 10% | 10% |
| kaolin | 62% | 27% | — |

The active ingredient is well mixed with additives and the mixture is thoroughly ground in a suitable mill. Wettable powders which can be diluted with water to give suspensions of the required concentration are obtained.

| 5. Emulsion concentrate | |
|---|---|
| active ingredient | 10% |
| octylphenol polyethylene glycol ether (4-5 mols of ethylene oxide) | 3% |
| calcium dodecylbenzene sulfonate | 3% |
| castor oil polyglycol ether (36 mols of ethylene oxide) | 4% |
| cyclohexanone | 30% |
| xylene mixture | 50% |

Emulsions of the concentration required can be obtained from this concentrate by dilution with water.

| 6. Dusts | (a) | (b) |
|---|---|---|
| active ingredient | 5% | 8% |
| talcum | 95% | — |
| kaolin | — | 92% |

Dusts ready for use are obtained by mixing the active ingredient with the carriers, ans grinding the mixture in a suitable mill.

| 7. Extruder granulate | |
|---|---|
| active ingredient | 10% |
| sodium lignin sulfonate | 2% |
| carboxymethyl cellulose | 1% |
| kaolin | 87% |

The active ingredient is mixed and ground with the additives, and the mixture is moistened with water. This mixture is extruded, granulated, and then dried in a stream of air.

| 8. Coated granulate | |
|---|---|
| active ingredient | 3% |
| polyethylene glycol (M.W. 200) | 3% |
| kaolin | 94% |

The finely ground active ingredient is evenly applied, in a mixer, to the kaolin moistened with polyethylene glycol. Dustfree coated granules are obtained in the manner.

| 9. Suspension concentrate | |
|---|---|
| active ingredient | 40% |
| ethylene glycol | 10% |
| nonylphenolpolyethylene glycol ether (15 mols of ethylene oxide) | 6% |
| sodium lignin sulfonate | 10% |
| carboxymethyl cellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the additives. There is obtained a suspension concentrate from which can be produced, by dilution with water, suspensions of the concentration required.

EXAMPLE 1

PRODUCTION OF 3-DIACETYLAMINOBENZISOTHIAZOLE

A mixture consisting of 11.7 g of 3-aminobenzisothiazole, 126 ml of acetanhydride and 0.2 g of sodium acetate is stirred for 48 hours at 100°–110? C. After concentration by evaporation and then chromatography (silica gel; eluant: hexane/diethyl ether 2:1), the product is recrystallised from hexane/diethyl ether to thus obtain the compound No. 1 of the formula

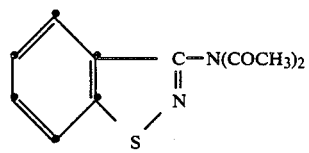

having a melting point of 65°–67° C.

The following compounds are produced in an analogous manner:

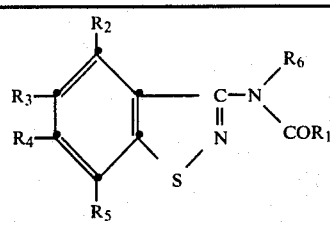

| No. | R₁ | R₂ | R₃ | R₄ | R₅ | R₆ | Physical data |
|---|---|---|---|---|---|---|---|
| 2 | —CH$_3$ | Cl | H | H | H | —COCH$_3$ | m.p.: 107–109° C. |
| 3 | —CH$_3$ | Cl | H | H | —NO$_2$ | H | m.p.: 193° C. |
| 4 | —C$_3$H$_{7(n)}$ | Cl | H | H | H | —COC$_3$H$_{7(n)}$ | m.p.: 76–80° C. |
| 5 | —C$_2$H$_5$ | Cl | H | H | H | —COC$_2$H$_5$ | m.p.: 101–103° C. |
| 6 | —CH$_2$Cl | Cl | H | H | H | —COCH$_2$Cl | m.p.: 118–119° C. |
| 7 | —CF$_2$CF$_3$ | Cl | H | H | H | H | m.p.: 98–99° C. |
| 8 | —CF$_3$ | Cl | H | H | H | H | m.p.: 127–129° C. |
| 9 | —CF$_2$CF$_2$CF$_3$ | Cl | H | H | H | H | m.p.: 97–98° C. |
| 10 | —CF$_3$ | —CH$_3$ | H | H | H | H | |
| 11 | —CH$_3$ | —OCH$_3$ | H | H | H | —COCH$_3$ | |
| 12 | (fused ring) | Cl | | H | H | H | —COCH$_3$ |
| 13 | (fused ring) | Cl | | H | H | H | H |

EXAMPLE 2

INSECTICIDAL CONTACT ACTION: *APHIS CRACCIVORA*

Plants (*Vicia fabae*) grown in pots are each infested before commencement of the test with about 200 individuals of the species *Aphis craccivora*. The plants infested in this manner are sprayed dripping wet 24 hours later with solutions containing 3, 12.5, 50 and 100 ppm, respectively, of the compound to be tested. Two plants are used per test compound and per concentration, and an evaluation of the mortality rate achieved is made after a further 24 hours.

The compounds according to Example 1 exhibit in the above test, against insects of the species *Aphis craccivora*, the activity shown in the Table which follows.

EXAMPLE 3

Insecticidal action (systemic): *Aphis craccivora*

Rooted bean plants are transplanted to pots each containing 600 ccm of soil; and 50 ml of a solution of the compound to be tested (obtained from a 25% wettable powder) at a concentration of 3, 12.5, 50 and 100 ppm, respectively, are subsequently poured directly onto the soil in each case. After 24 hours, aphids of the species *Aphis craccivora* are settled onto the parts of the plants above the soil, and a plastics cylinder is placed over each plant and drawn to by tying at the bottom in order to protect the aphids from any contact or gas action of the test substance. An evaluation of the mortality rate achieved is made 48 and 72 hours after commencement of the test. Two plants, each in a separate pot, are used per concentration level of test substance. The test is carried out at 25° C. with 70% relative humidity.

The compounds according to Example 1 exhibit in the above test, against insects of the species *Aphis craccivora*, the systemic activity shown in the following Table.

Biological test results

In the following Table are summarised test results based on the Examples given in the foregoing, the index of values with regard to the percentage mortality of the pests being as follows:

A: 70–100% mortality with 3 ppm of active ingredient

B: 70–100% mortality with 12.5 ppm of active ingredient

C: 70–100% mortality with 50 ppm of active ingredient

D: 70–100% mortality with 100 ppm of active ingredient.

| Compound No. | Contact action against *Aphis craccivora* | Systemic action against *Aphis craccivora* |
|---|---|---|
| 1 | A | A |
| 2 | B | C |
| 3 | B | B |
| 4 | B | B |
| 5 | A | A |
| 6 | A | B |
| 7 | B | B |
| 8 | A | B |
| 9 | A | B |

What is claimed is:

1. A method of controlling insects, and members of the order Acarina on animals and plants and in the soil, which method comprises applying thereto or to the locus thereof an insecticidally effective amount of a compound of the formula I

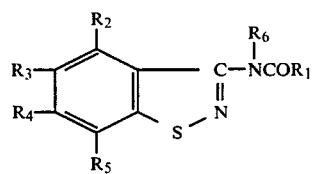

wherein $R_1$ is $C_1$–$C_3$-alkyl, unsubstituted or substituted by halogen or phenyl, $R_2$, $R_3$, $R_4$ and $R_5$ independently of one another are each hydrogen, halogen, $C_1$–$C_5$-alkyl, $C_1$–$C_5$-alkoxy, trifluoromethyl, amino or nitro, and $R_6$ is hydrogen or —$COR_1$.

2. A 3-acylaminobenzisothiazole of the formula

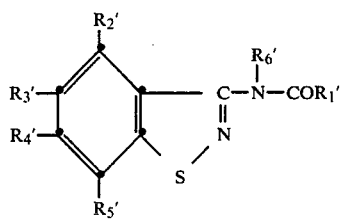

(Ia)

wherein
$R_1'$ is $C_1$–$C_3$-perfluoroalkyl
$R_2'$, $R_3'$, $R_4'$ and $R_5'$ independently of one another are each hydrogen, chlorine, trifluoromethyl, amino or nitro, and $R_6'$ is hydrogen or —$COR_1'$ 3. The compound according to claim 2 of the formula

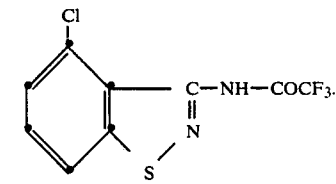

4. the compound according to claim 2 of the formula

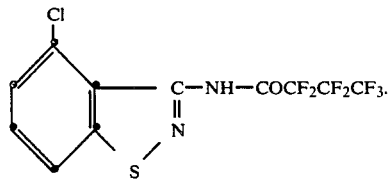

5. The compund according to claim 2 of the formula

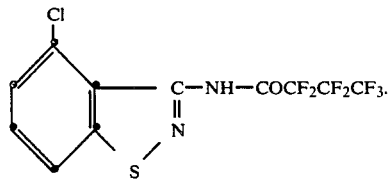

* * * * *